United States Patent
Benke et al.

(10) Patent No.: US 10,613,248 B2
(45) Date of Patent: Apr. 7, 2020

(54) PASSIVE ALERTING AND LOCATING SYSTEM

(71) Applicant: Alert R&D, LLC, Austin, TX (US)

(72) Inventors: Roland R. V. Benke, Austin, TX (US); David M. Hamby, Corvallis, OR (US)

(73) Assignee: ALERT R&D, LLC, Austin, TX (US)

( * ) Notice: Subject to any disclaimer, the term of this patent is extended or adjusted under 35 U.S.C. 154(b) by 99 days.

(21) Appl. No.: 15/792,706

(22) Filed: Oct. 24, 2017

(65) Prior Publication Data

US 2019/0120997 A1    Apr. 25, 2019

(51) Int. Cl.
| | | |
|---|---|---|
| *G01V 5/00* | (2006.01) | |
| *G01T 1/167* | (2006.01) | |
| *A61B 5/00* | (2006.01) | |
| *G08B 21/12* | (2006.01) | |
| *G21F 3/02* | (2006.01) | |
| *G01T 1/29* | (2006.01) | |
| *G08B 6/00* | (2006.01) | |

(52) U.S. Cl.
CPC .......... *G01V 5/0075* (2013.01); *A61B 5/7455* (2013.01); *G01T 1/167* (2013.01); *G01T 1/2907* (2013.01); *G08B 6/00* (2013.01); *G08B 21/12* (2013.01); *G21F 3/02* (2013.01)

(58) Field of Classification Search
CPC ...... G01V 5/0075; A61B 5/7455; G01T 1/167
See application file for complete search history.

(56) References Cited

U.S. PATENT DOCUMENTS

| | | | |
|---|---|---|---|
| 3,454,770 A | 7/1969 | Cialella | |
| 3,951,550 A | 4/1976 | Slick | |
| 4,197,461 A * | 4/1980 | Umbarger | G01T 1/24 250/370.07 |
| 4,804,848 A | 2/1989 | Horiba | |
| 5,045,700 A | 9/1991 | Crowson | |
| 5,274,238 A * | 12/1993 | Brown | G01T 1/16 250/394 |
| 5,959,451 A | 9/1999 | De Torfino | |
| 6,198,394 B1 | 3/2001 | Jacobsen | |
| 6,255,658 B1 * | 7/2001 | Ozil | G01T 1/169 250/253 |
| 6,433,335 B1 | 8/2002 | Kronenberg | |
| 6,774,769 B2 | 8/2004 | Okada | |
| 7,064,333 B2 | 6/2006 | Torii | |
| 7,321,121 B2 | 1/2008 | Testardi | |
| 7,387,276 B1 | 6/2008 | Smith | |
| 7,391,028 B1 | 6/2008 | Rubenstein | |
| 7,595,494 B2 | 9/2009 | Koltick | |
| 7,655,912 B2 | 2/2010 | Shirakawa | |

(Continued)

OTHER PUBLICATIONS

PCT International Search Report, dated Jan. 28, 2019, 15 pages.

(Continued)

*Primary Examiner* — David P Porta
*Assistant Examiner* — Jeremy S Valentiner

(57) ABSTRACT

According to one general aspect, an apparatus may include a plurality of sensors configured to detect a presence of a source of radiation. The apparatus may include a garment configured to be worn by a user. The garment may include a plurality of tactile feedback devices configured to automatically indicate to the user, without intervention by the user, a direction of the source of radiation.

20 Claims, 9 Drawing Sheets

(56) References Cited

U.S. PATENT DOCUMENTS

| | | | |
|---|---|---|---|
| 7,864,061 B2* | 1/2011 | Frank | G01T 1/167 250/363.04 |
| 7,994,926 B2 | 8/2011 | Longman | |
| 8,552,847 B1* | 10/2013 | Hill | G06F 3/016 340/407.1 |
| 8,890,079 B2 | 11/2014 | Kurochi | |
| 2004/0004573 A1* | 1/2004 | Apostolos | G01S 5/04 343/718 |
| 2004/0204915 A1 | 10/2004 | Steinthal | |
| 2005/0104773 A1 | 5/2005 | Clarke | |
| 2008/0048123 A1 | 2/2008 | Larsson | |
| 2008/0120029 A1* | 5/2008 | Zelek | G01C 21/20 701/469 |
| 2009/0073112 A1 | 3/2009 | Basson | |
| 2011/0153197 A1* | 6/2011 | Song | A61B 5/1038 701/533 |
| 2012/0176237 A1* | 7/2012 | Tabe | A61B 5/6804 340/539.12 |
| 2013/0049957 A1* | 2/2013 | Seki | G01C 21/3652 340/539.13 |
| 2014/0190266 A1 | 7/2014 | Strozier | |
| 2014/0206948 A1 | 7/2014 | Romem | |
| 2014/0263989 A1 | 9/2014 | Landauer | |
| 2015/0065081 A1 | 5/2015 | Estes | |
| 2015/0065082 A1 | 5/2015 | Sehgal | |
| 2016/0038083 A1* | 2/2016 | Ding | A61B 5/6804 600/388 |
| 2016/0267755 A1* | 9/2016 | Martinson | G08B 6/00 |

OTHER PUBLICATIONS

Rebecca Boyle, Haptic Vibrating Belts Guide U.S. Soldiers Through the Darkness, Popular Science, Jun. 28, 2011, http://www.popsci.com/technology/article/2011-06/new-haptic-system-guides-us-soldiers-through-darkness.

Precision Microdevices, AB-010: Mounting Vibration Motors to Flexible Materials & Clothing, https://www.precisionmicrodrives.com/application-notes/ab-010-mounting-vibration-motors-to-flexible-materials-clothing, printed Oct. 8, 2017.

Andreas Riener and Alois Ferscha, Raising Awareness about Space via Vibro-Tactile Notifications, D. Roggen et al. (Eds.): EuroSSC 2008, LNCS 5279, pp. 235-245, 2008.

David Curry, Fitbit hit with lawsuit over haptic feedback patents, Jul. 21, 2017, https://readwrite.com/2017/07/21/fitbit-patent-lawsuit-hl1/.

* cited by examiner

PASSIVE ALERTING AND LOCATING SYSTEM

TECHNICAL FIELD

This description relates to threat detection and positioning, and more specifically to a system for passive nuclear, biological, or chemical detection and positioning.

BACKGROUND

Law enforcement (LE) agencies of large cities in the United States often use a variety of personal radiation detectors (PRDs) for routine surveillance and first-responder radiological assessments. These PRDs are typically units that are worn on the duty belt of a law enforcement officer (LEO) with a readout of exposure rate and alarm capabilities to alert the officer if they are entering a high-radiation area.

These existing systems may be inconvenient for at least two reasons. First, when the PRD alarms, the LEO must divert their attention to the device, read, and interpret its output display, and determine appropriate next steps. This diversion of attention and having to hold an object, is quite dangerous for a law enforcement officer. Most officers will state that this scenario puts them at a great tactical disadvantage. Further, monitoring the PRD's readings is not only noticeable to others, but also reveals plain-clothed officers.

Second, the typical PRD has no means of detecting the location of the radiation source. With a PRD, the LEO reads its display for an assessment of exposure at their location, but the unit typically gives no information whatsoever so as to provide a means of locating the radiation source and, if co-located, the potential offenders. As such, without this directional or positional information the officer is generally unable to relocate civilians to a safe area and begin a search, if necessary.

SUMMARY

According to one general aspect, an apparatus may include a plurality of sensors configured to detect a presence of a source of radiation. The apparatus may include a garment configured to be worn by a user. The garment may include a plurality of tactile feedback devices configured to automatically indicate to the user, without intervention by the user, a direction of the source of radiation.

According to another general aspect, a system may include a plurality of sensors configured to detect a presence of, at least one of, a source of contamination. The system may also include a processing circuit configured to determine a level of baseline contamination level. The system may further include a plurality of tactile feedback devices configured to: be worn by a user, and automatically, and at least partially passively, indicate to the user a direction of the source of contamination.

According to another general aspect, a system may include a plurality of passive radiation alerting and locating systems, each passive radiation alerting and locating system, at least partially, worn by a respective user. Wherein each passive radiation alerting and locating system may include: a plurality of sensors configured to detect a direction of a source of radiation, a processing circuit configured to determine a level of baseline radiation and control, at least in part, a plurality of tactile feedback devices, and the plurality of tactile feedback devices configured to automatically, and at least partially passively, indicate to the user the direction of the source of radiation. Wherein the plurality of passive radiation alerting and locating systems are configured to communicate detection information amongst one another.

The details of one or more implementations are set forth in the accompanying drawings and the description below. Other features will be apparent from the description and drawings, and from the claims.

A system and/or method for threat detection and positioning, and more specifically to a system for passive nuclear, biological, or chemical detection and positioning, substantially as shown in and/or described in connection with at least one of the figures, as set forth more completely in the claims.

BRIEF DESCRIPTION OF THE DRAWINGS

Like reference symbols in the various drawings indicate like elements.

DETAILED DESCRIPTION

Figure 1:
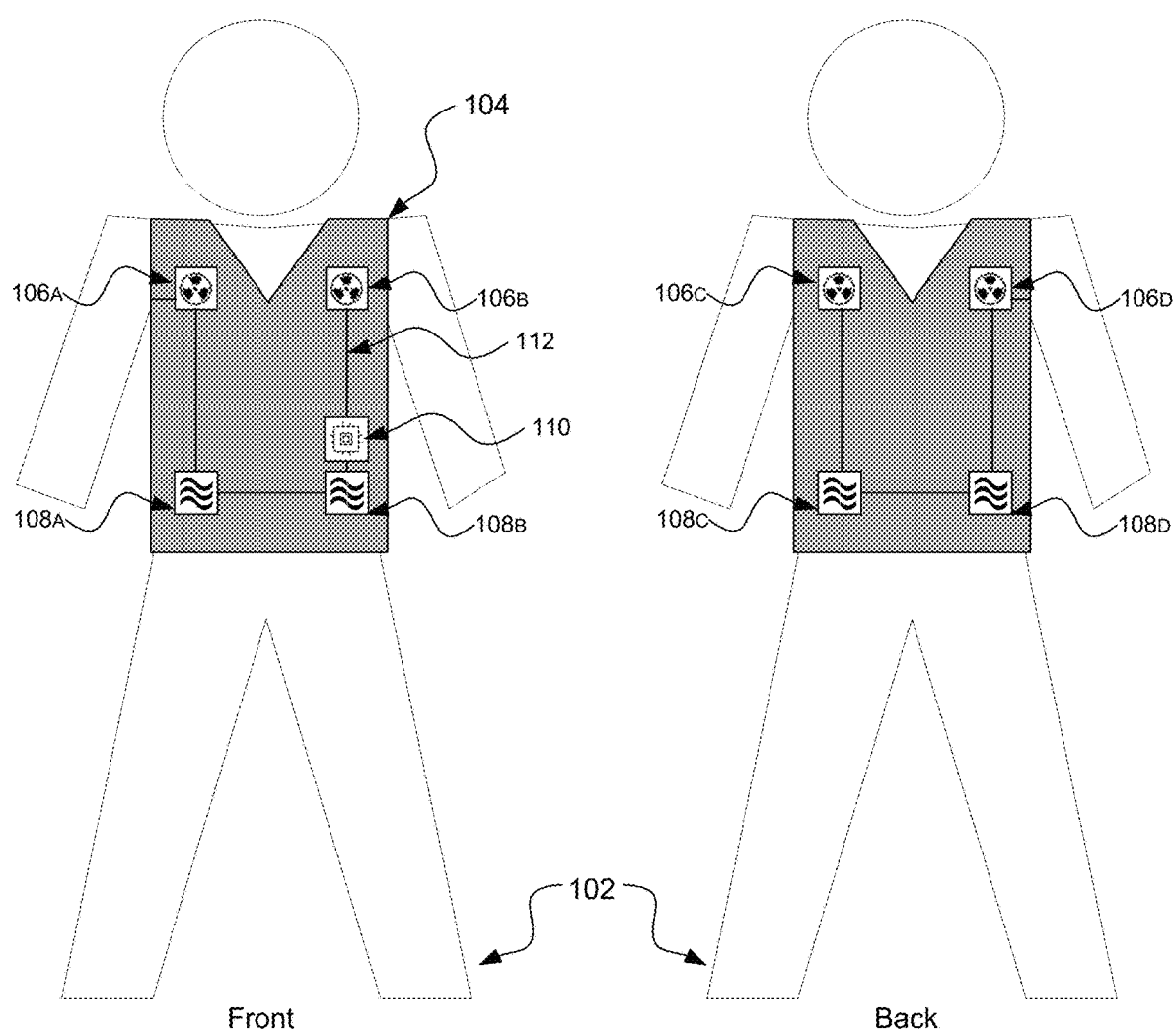
FIG. 1 is a diagram of an example embodiment of a system in accordance with the disclosed subject matter.

Various example embodiments will be described more fully hereinafter with reference to the accompanying drawings, in which some example embodiments are shown. The present disclosed subject matter may, however, be embodied in many different forms and should not be construed as limited to the example embodiments set forth herein. Rather, these example embodiments are provided so that this disclosure will be thorough and complete, and will fully convey the scope of the present disclosed subject matter to those skilled in the art. In the drawings, the sizes and relative sizes of layers and regions may be exaggerated for clarity.

It will be understood that when an element or layer is referred to as being "on," "connected to" or "coupled to" another element or layer, it may be directly on, connected or coupled to the other element or layer or intervening elements or layers may be present. In contrast, when an element is referred to as being "directly on", "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, and so on may be used herein to describe various elements, components, regions, layers and/or sections, these elements, components, regions, layers and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of the present disclosed subject matter.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" may encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present disclosed subject matter. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the exact shape of a region of a device and are not intended to limit the scope of the present disclosed subject matter.

Unless otherwise defined, all terms (including technical and scientific terms) used herein have the same meaning as commonly understood by one of ordinary skill in the art to which this disclosed subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

FIG. 1 is a diagram of an example embodiment of a system 100 in accordance with the disclosed subject matter. In various embodiments, the system may be worn, used, or employed by law enforcement (LE), by the military, by other government agents, or by civilians. In such an embodiment, the system 100 may facilitate the detection and location of one or more substances (e.g., a radiation source).

In the illustrated embodiment, a garment 104 may be worn by a user 102. In various embodiments, the garment 104 may be a vest (e.g., a ballistic vest, bulletproof vest, tactical vest, etc.) or another form of clothing (e.g., helmet, pants, jacket, wristbands, chest band or belt, etc.). It is understood that the above is merely one illustrative example to which the disclosed subject matter is not limited.

In such an embodiment, the system 100 may be configured to automatically detect a source of radiation or other substance. The system 100 may then automatically indicate to the user 102 the direction toward the detected source of radiation or other sub stance.

In various embodiments, the system 100 may be configured to detect one or more forms of nuclear, biological, or chemical (NBC) substances. In various embodiments, the terms chemical, biological, and radiological (CBR) or chemical, biological, radiological, nuclear, or explosives (CBRNE) may also be used. In some embodiments, these NBC substances may be threats or hazards. For example, a chemical agent (e.g., chemical warfare agents (CWAs), toxic industrial chemicals (TICs), explosives, etc.) may be detected. In another embodiment, the radiation (e.g., particle radiation, electromagnetic radiation, ionizing radiation, etc.) of a weapon, device, or substance may be detected. In other embodiments, the system 100 may be configured to detect biological agents (e.g., airborne spore, viral, cellular, and protein toxins, etc.). In yet another embodiment, the chemical signature of an illegal drug (e.g., narcotics, etc.) may be detected. It is understood that the above are merely a few illustrative examples to which the disclosed subject matter is not limited.

In the illustrated embodiment, the system 100 may include a plurality of detectors or sensors 106 (sensors 106A, 106B, 106C, and 106D). In the illustrated embodiment, the sensors 106 may be configured to detect radiation. In one embodiment, this may be ionizing radiation. It is understood that the above is merely one illustrative example to which the disclosed subject matter is not limited.

In various embodiments, the plurality of sensors 106 may be distributed across the garment 104 in a constellation or arrangement that facilitates detection of radiation in multiple directions. In the illustrated embodiment, the sensor 106A is placed on the upper right of the front of the garment 104. The sensor 106B is placed on the upper left of the front of the garment 104. The sensor 106C is placed on the upper left of the back of the garment 104. The sensor 106D is placed on the upper right of the back of the garment 104. In such an embodiment, each sensor 106 may detect a radiation source from one of four directions. In such an embodiment, the sensors 106 themselves may not include directional sensing, but may be arranged in the system 100 in such a way that the system 100 provides or determines a directional component in the information provided by the sensors 106. In another embodiment, the sensors 106 themselves may include a directional aspect. It is understood that the above is merely one illustrative example to which the disclosed subject matter is not limited.

As described below in reference to FIGS. 6 and 7, for radiation detection the sensor 106 closest to the source of the radiation may receive more radiation than the other sensors. For example, if the source of radiation is near the user 102's front right, the sensor 106A (front right) may receive the most radiation, whereas sensor 106C (back left, and blocked by the user 102's body) may receive the least radiation. In such an embodiment, the constellation of sensors 106 may be configured to determine or provide information that helps to determine where, relative to the user 102, the radiation source is located.

In the illustrated embodiment, the system 100 may include a plurality of tactile feedback devices 108 (e.g., tactile feedback devices 108A, 108B, 108C, and 108D). In various embodiments, these tactile feedback devices 108 may be configured to automatically indicate to the user 102 the direction of the source of radiation or other detected source.

In various embodiments, the tactile feedback devices 108 may be arranged in a constellation to provide tactile feedback in a plurality of directions. In the illustrated embodiment, the tactile feedback device 108A may be placed on the lower right of the front of the garment 104. The tactile feedback device 108B is placed on the lower left of the front of the garment 104. The tactile feedback device 108C is placed on the lower left of the back of the garment 104. The tactile feedback device 108D is placed on the lower right of the back of the garment 104. It is understood that the above is merely one illustrative example to which the disclosed subject matter is not limited.

As described above, the tactile feedback devices 108 may be configured to automatically indicate to the user 102 the direction toward the source of radiation or other detected source. In one embodiment, this may be done passively or without active user intervention. For example, in such an embodiment, if a radiation source is detected the tactile feedback devices 108 may vibrate, light up, emit a noise, or otherwise indicate that the radiation source has been detected. This contrasts with existing personal radiation detectors (PRDs) that require the user 102 to manually hold the PRD and then look at the PRD's display screen to check whether or not a radiation source has been detected. Existing PRDs also have severe limitations for determining the direction of a radiation source.

In various embodiments, the tactile feedback devices 108 may be configured to provide feedback or an indication in a way that, at least partially, informs the user 102 of the direction toward the radiation source. For example, as described above, if the radiation source is located towards the user 102's front right, only the tactile feedback device 108A may vibrate (or otherwise provide feedback). Likewise, if the radiation source is directly behind the user 102, both tactile feedback devices 108C and 108D may vibrate. From these vibrations (e.g., only in the front right, or directly behind the user, etc.) the user 102 may quickly determine in which direction, relative to the user 102's body, the radiation source is located. It is understood that the above are merely a few illustrative examples to which the disclosed subject matter is not limited.

In such an embodiment, the tactile feedback devices 108 may be configured to vary their intensity or reaction based upon the strength of the detected radiation source. Accepting readings from the plurality of sensors 106, a processor 110 can control the tactile feedback devices 108, and the processor 110 can have variable sensitivity settings. For example, the greater the amount of detected radiation, the greater the amount of vibration produced by tactile feedback devices 108. In another embodiment in which the feedback devices 108 may further emit a sound or noise, as the level of detected radiation changes, the pitch, frequency, volume, or tone of the emitted noise may change. Likewise, if the feedback devices 108 emit a light, as the level of detected radiation changes the color, brightness, frequency, or pattern of the light may change. In some embodiments, the change in the feedback may occur at steps or quantum levels. In another embodiment, the change in the feedback may be along a continuous spectrum of feedback responses. It is understood that the above are merely a few illustrative examples to which the disclosed subject matter is not limited.

In various embodiments, the sensors 106 and tactile feedback devices 108 may be configured to only alert a user 102 if the level of detected radiation exceeds a certain threshold. In various embodiments, that threshold may be adjustable, configurable, or based upon a background or baseline radiation level. In various embodiments, a plurality of thresholds may be employed. For example, if a first threshold is reached the tactile feedback devices 108 may vibrate at a first intensity. If a second threshold is then reached the tactile feedback devices 108 may increase their vibration to a second or higher intensity, and so on for the number of thresholds a particular embodiment of the system 100 may have. If the level of detected radiation does not exceed or falls below the desired threshold, the tactile feedback devices 108 may not vibrate or otherwise indicate the direction of the source of radiation. The system may consist of sensors 106 and feedback devices 108 that indicate the direction of radiation as well as the overall intensity or magnitude of the radiation field.

In various embodiments, the form of feedback may be silent or otherwise substantially undetectable by someone who isn't the user 102 (e.g., an innocent bystander). In another embodiment, the form of feedback may be silent at a first threshold level, and then non-silent or otherwise detectable by someone who isn't the user 102 (e.g., an innocent bystander) at a second threshold level. For example, if the radiation level is below a certain threshold, the tactile feedback devices 108 may (substantially) silently vibrate. But if the radiation level rises above a critical threshold, the tactile feedback devices 108 may begin to loudly sound an alarm. It is understood that the above are merely a few illustrative examples to which the disclosed subject matter is not limited.

In such embodiments, the system 100 may be configured to alert the user 102, without active intervention by the user 102, that a source of radiation has been detected. The system 100, via the intensity or other response of the tactile feedback devices 108, may indicate what the approximate strength or level of the detected radiation source is. The system 100, via the tactile feedback devices 108, may be configured to inform the user 102 of the general direction (e.g., front, back, left, right) of the detected radiation source. The system 100 may be configured to provide this information to the user 102 all without having to look at their PRD (which involves taking their eyes off their surroundings and may involve taking their hands off any weapon or other tool), and depending upon the form of tactile feedback, without alerting others (e.g., innocent bystanders, etc.) that a source of radiation (or other detected NBC source) has been detected.

In various embodiments, the system 100 may include a processing unit or circuit 110. In various embodiments, the processing circuit 110 may be configured to determine a level of background or baseline radiation. In such an embodiment, the processing circuit 110 may further adjust a detected level of radiation based, at least in part, upon the level of background or baseline radiation. In another embodiment, the processing circuit 110 may further adjust the threshold(s) based, at least in part, upon the level of background or baseline radiation. In such an embodiment, the processing circuit 110 may attempt to prevent the number of false positive detections encountered by the system 100.

For example, the level of background or baseline radiation detected in an airplane or a nuclear reactor may be high compared to the level of background or baseline radiation in an underground storage area or inside a building. In various embodiments, one of the uses of the system 100 may be to alert a user 102 when an unusual level of a radiation is detected. Therefore, the processing circuit 110 may increase the detection threshold(s) when in a place of high baseline radiation, and decrease (or refrain from increasing) the detection threshold(s) when in a place of low baseline radiation and accommodate adjustments for changes in background levels. In another embodiment, the processing circuit 110 may subtract the baseline level of radiation from the raw or unaltered level of radiation detected by the sensors 106. It is understood that the above are merely a few illustrative examples to which the disclosed subject matter is not limited.

In various embodiments, the user 102 may initiate a check, calibration, or setting of the background or baseline radiation level. For example, the user 102, at the beginning of their shift or when arriving at the place they will patrol, could cause the system 100 to check the level of radiation and use that to set the baseline radiation level. In another embodiment, the processing circuit 110 may automatically (e.g., periodically, based upon a location or distance travelled, etc.) check the baseline radiation level.

In various embodiments, the processing circuit 110 may be configured to read or accept as input the detected radiation levels from the various sensors 106. In some embodiments, the processing circuit 110 may be configured to adjust the raw detected radiation levels as desired. The processing circuit 110 may be configured to instruct the tactile feedback devices 108 how to react, based upon the detected radiation levels. For example, if the radiation is detected towards the front right and exceeds a minimum threshold, the processing circuit 110 may instruct or cause the tactile feedback device 108A to vibrate. If the detected radiation level is detected towards the front right and exceeds an alert threshold, the processing circuit 110 may instruct the tactile feedback device 108A to vibrate with great intensity or emit a light.

In the illustrated embodiment, the system 100 may communicate between the sensors 106, tactile feedback devices 108, and the processing circuit 110 via a bus or communications link 112. In various embodiments, the communications link 112 may include a wired connection, wireless connection, or a combination thereof. In the illustrated embodiment, this communication link 112 may be coupled with all of the elements of system 100. In another embodiment, multiple communication links 112 or groupings thereof may be employed and connect only to respective subgroups of the elements of system 100 (e.g., a subgroup for the front, a subgroup of the sensors 106, etc.).

In various embodiments, the processing circuit 110 may include an electronic circuit, an integrated circuit, a dedicated computer processing unit, personal digital assistant, smartphone, tablet, or other appropriate computing device. In various embodiments, one or more of the sensors 106, tactile feedback devices 108, and/or processing circuit 110 may be integrated with or separated from one another. In various embodiments, one or more of the sensors 106, tactile feedback devices 108, and/or processing circuit 110 may be integrated with or fixedly mounted to the garment 104. In another embodiment, one or more of the sensors 106, tactile feedback devices 108, and/or processing circuit 110 may be removably mounted or stored within the garment 104. For example, in one embodiment, the processing circuit 110 may be placed with a pouch or pocket of the garment 104 such that a user 102 may temporarily remove it and innate the setting of the baseline radiation. It is understood that the above is merely one illustrative example to which the disclosed subject matter is not limited.

Figure 2:
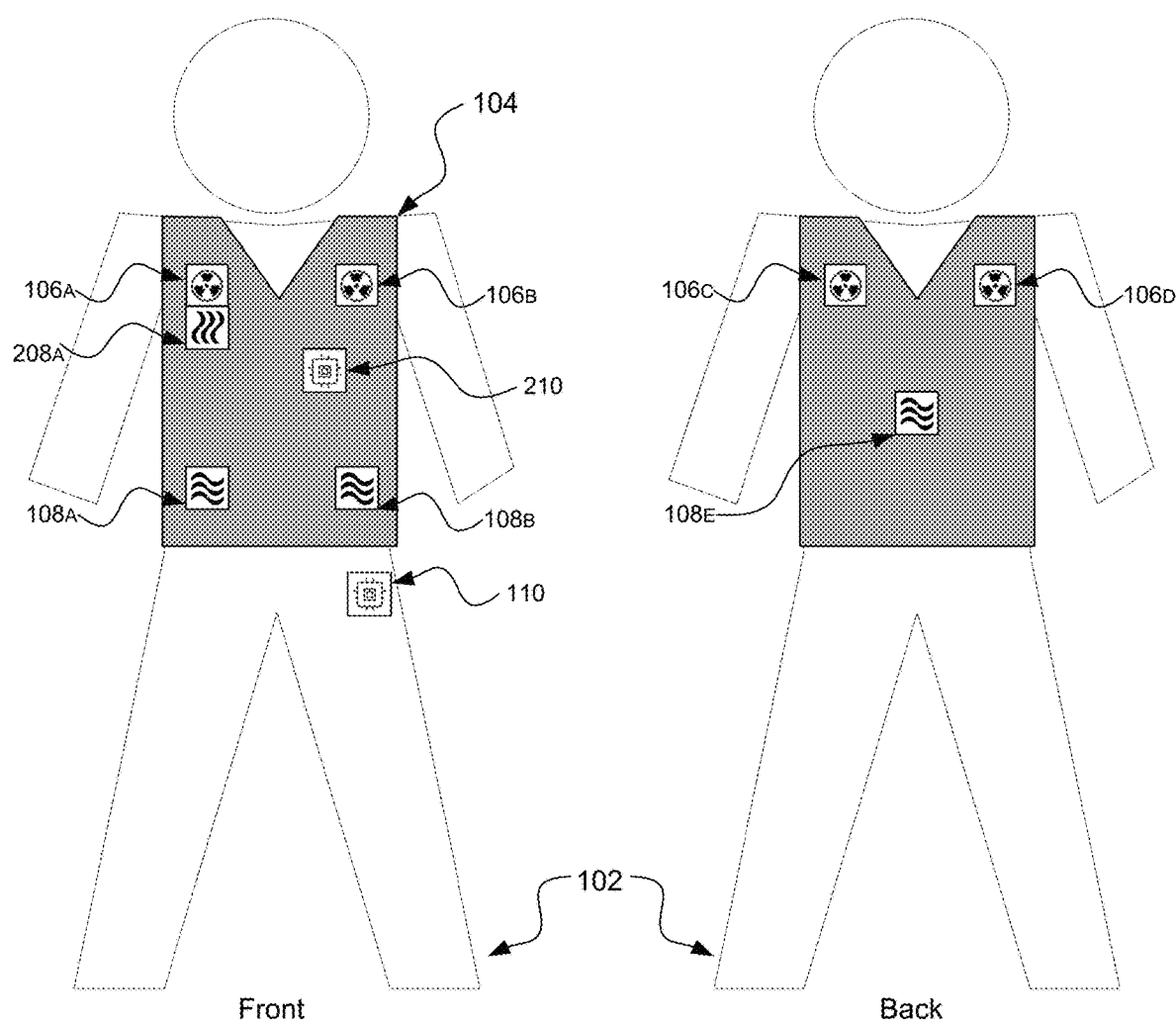
FIG. 2 is a diagram of an example embodiment of a system in accordance with the disclosed subject matter.

FIG. 2 is a diagram of an example embodiment of a system 200 in accordance with the disclosed subject matter. In various embodiments, the system may be worn, used, or employed by law enforcement (LE), by the military, by other government agents, or by civilians. In such an embodiment, the system 200 may facilitate the detection and location of one or more substances (e.g., a radiation source).

As described above, the system 200 may be worn or employed by a user 102. The system 200 may include a garment 104, a plurality of sensors 106 (e.g., sensors 106A, 106B, 106C, and 106D), a plurality of tactile feedback devices 108 (e.g., devices 108A, 108B, and 108E), and processing device 110. It is understood that the above are merely a few illustrative examples to which the disclosed subject matter is not limited.

In the illustrated embodiment, it is shown that the number of sensors 106 and the number of tactile feedback devices 108 need not be that same. In the illustrated embodiment, there may be four sensors 106 (arranged in a rough square shaped constellation) and only three tactile feedback devices 106 (arranged in a rough triangle shaped constellation). In such an embodiment, the tactile feedback devices 108A and 108B may be placed on the front, lower, right and left of the user 102, and the tactile feedback devices 108E may be placed in middle of the user 102's back. It is understood that the above is merely one illustrative example to which the disclosed subject matter is not limited.

In such an embodiment, the processing circuit 110 may be configured to map the directional input (various levels of detected radiation) from the sensors 106 to the directional output or feedback points of the tactile feedback devices 108.

In the illustrated embodiment, the system 200 may include a secondary or alert feedback device 208A (e.g. placed on the user 102's front, right shoulder). In some embodiments, if the strength of the detected radiation source exceeds an alert threshold the system 200 may provide a special or alert indication. For example, if the tactile feedback devices 108 generally provide feedback via vibration, a secondary or different form of feedback may be employed by the alert feedback device 208A (e.g., light).

In such an embodiment, if an alert threshold is exceeded the alert feedback device 208A may also provide feedback (e.g., via light). In the illustrated embodiment, the alert feedback device 208A may be mounted such that the user 102 can see the light in their peripheral vision without taking an active step (e.g., raising the PRD to their face and looking at the PRD).

In various embodiments, the tactile feedback devices 108 may include this alert notification feature and/or multiple types of feedback (e.g., vibration and light). In some embodiments, a plurality of alerts may be employed (e.g., low, medium, high) with various respective outputs or forms of feedback. It is understood that the above are merely a few illustrative examples to which the disclosed subject matter is not limited.

In various embodiments, the processing circuit 110 may not be coupled with the garment 104. For example, in one embodiment, if the processing circuit 110 includes a smartphone, tablet, or form of PRD, the user 102 may not store or attach the processing circuit 110 to the garment 104. In such an embodiment, the processing circuit 110 may communicate with the sensors 106 and feedback devices 108 and 208 via a communications circuit 210. In such an embodiment, the communications circuit 210 may be mounted or coupled with the garment 104. In various embodiments, multiple communications circuits 210 may be employed, and those communications circuits 210 may be integrated with the sensors 106 and/or feedback devices 108 and 208.

Figure 3:
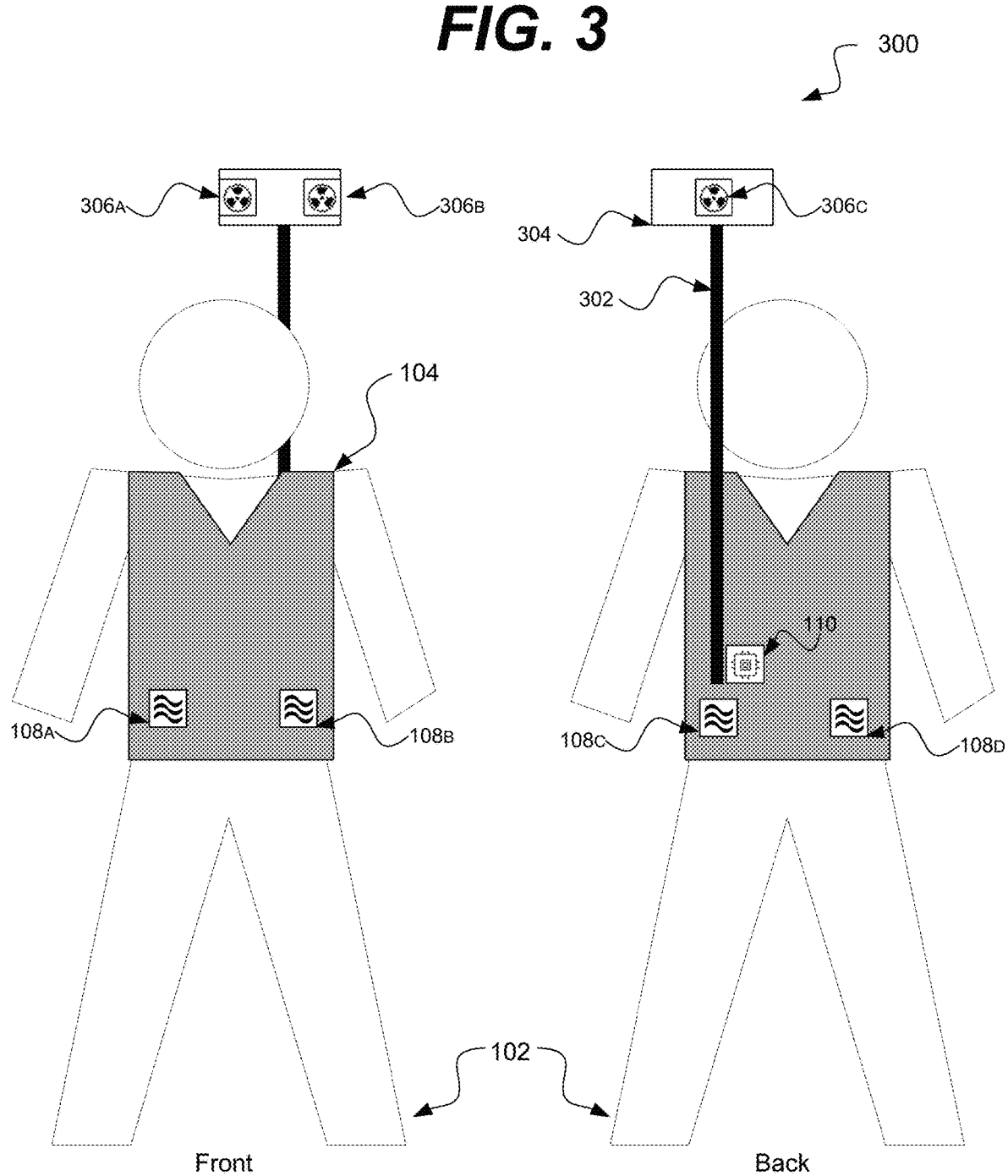
FIG. 3 is a diagram of an example embodiment of a system in accordance with the disclosed subject matter.

FIG. 3 is a diagram of an example embodiment of a system 300 in accordance with the disclosed subject matter. In various embodiments, the system may be worn, used, or employed by law enforcement (LE), by the military, by other government agents, or by civilians. In such an embodiment, the system 300 may facilitate the detection and location of one or more substances (e.g., a radiation source).

As described above, the system 300 may be worn or employed by a user 102. The system 300 may include a garment 104, a plurality of sensors 306 (e.g., sensors 306A, 306B, and 306C), a plurality of tactile feedback devices 108 (e.g., devices 108A, 108B, 108C, and 108D), and processing device 110. It is understood that the above is merely one illustrative example to which the disclosed subject matter is not limited.

In various embodiments, the sensors 306 may be detached or removed from the main portion of the garment 104. In various embodiments, additional sensors (not shown) may be coupled with the garment as shown in FIGS. 1 and 2.

In the illustrated embodiment, the sensors 306 may be coupled with a sensor pod 304. In turn, the sensor pod 304 may be coupled with a pole or rod 302. In such an embodiment, the rod 302 may elevate at least a portion of the sensors 306 (and sensor pod 304) above a head of the user 102. In such an embodiment, the sensors 306 may be raised to provide a better radiological view, compared to mounting the sensors 306 on the garment 104. In such an embodiment, this may allow the sensors 306 to not be blocked by a crowd of people or other mass. It is understood that the above are merely a few illustrative examples to which the disclosed subject matter is not limited.

In various embodiments, if multiple sensors 306 are placed on the sensor pod 304, they may be separated by sufficient shielding to allow differential detection techniques. In such an embodiment, each sensor 306 may be associated with a different direction or position and may be separated (either physically or by shielding) enough for multiple directions or positions to be discernable.

In various embodiments, the rod 302 may be coupled with the garment 104. In another embodiment, the rod 302 and sensor pod 304 may be detachable or placed on another device, vehicle, or mechanical conveyance (e.g., a motorcycle, drone, etc.).

In yet another embodiment, the system 300 may not include a rod 302 but only the sensor pod 304. For example, a drone (not shown) may include or be coupled with sensor pod 304 and may be programmed to hover above and follow the user 102. In one such embodiment, the sensor pod 304 may hang from the drone by the rod 302. In such an embodiment, the sensor pod 304 may not remain at a constant position relative to the user 102, either in terms of distance or direction. Instead, the drone (and sensor pod 304) may be configured to stay within a radius or distance of the user 102 and may rotate (in respect to the user 102's orientation) as directed or as necessary as part of the flight parameters of the drone. It is understood that the above are merely a few illustrative examples to which the disclosed subject matter is not limited.

In such an embodiment, the processing circuit 110 may be configured to dynamically adjust the mapping between the sensors 306 and the tactile feedback devices 108 just that associated directions of the sensors 306 are aligned with the directions of the tactile feedback devices 108. In various embodiments, the processing circuit 110 may be coupled with the rod 302, the sensor pod 304, and/or the garment 104.

Figure 4:
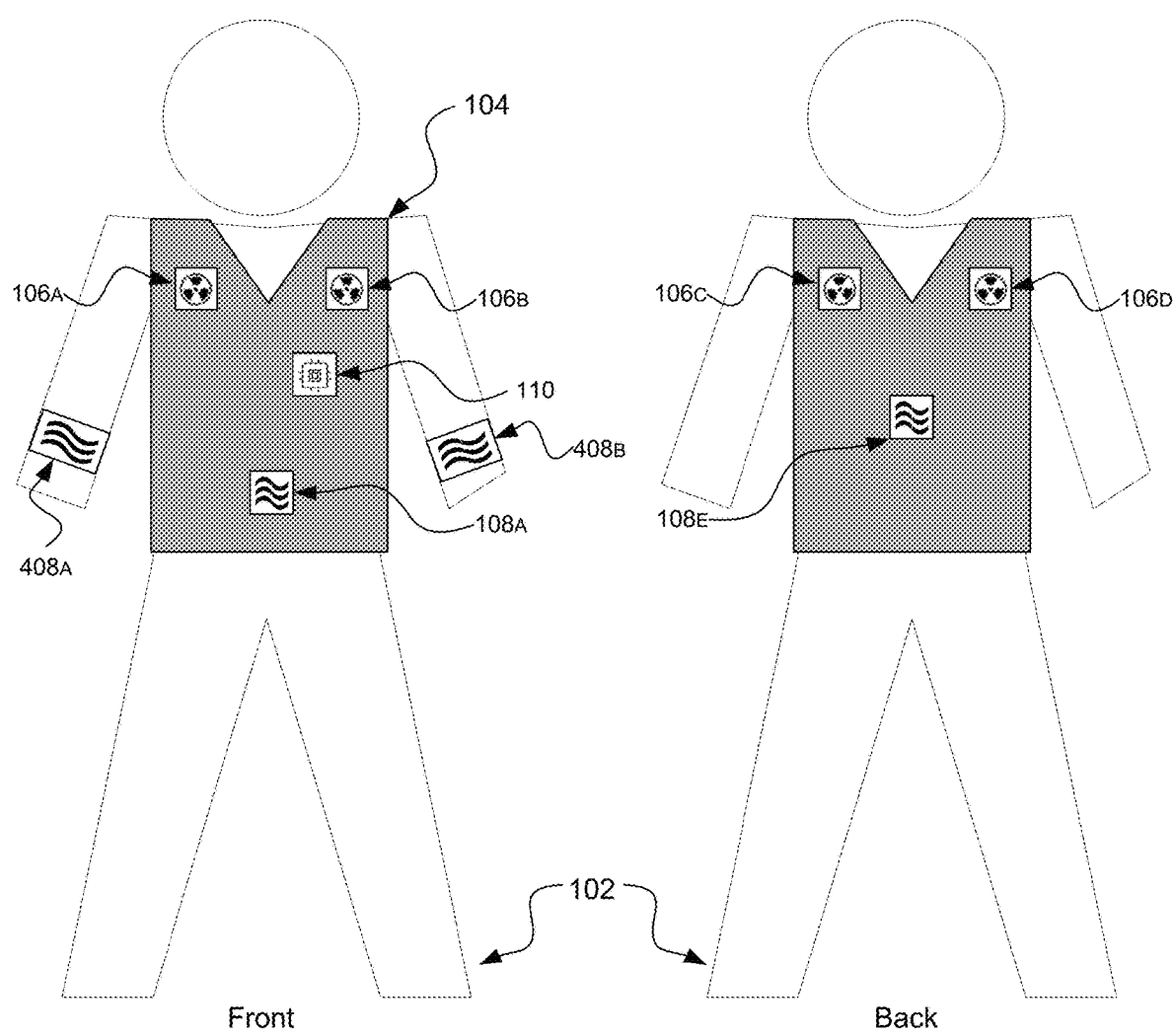
FIG. 4 is a diagram of an example embodiment of a system in accordance with the disclosed subject matter.

FIG. 4 is a diagram of an example embodiment of a system 400 in accordance with the disclosed subject matter. In various embodiments, the system may be worn, used, or employed by law enforcement (LE), by the military, by other government agents, or by civilians. In such an embodiment, the system 400 may facilitate the detection and location of one or more substances (e.g., a radiation source).

As described above, the system 400 may be worn or employed by a user 102. The system 400 may include a garment 104, a plurality of sensors 106 (e.g., sensors 106A, 106B, 106Cm and 106D), a plurality of tactile feedback devices 108 and 408 (e.g., devices 108A, 108E, 408A, and 408B), and processing circuit 110. It is understood that the above is merely one illustrative example to which the disclosed subject matter is not limited.

In various embodiments, the system 400 may include tactile feedback devices 408 that are detached from the garment 104. In the illustrated embodiment, the tactile feedback devices 408A and 408B may be worn on the user 102's right and left wrists or arms. In various embodiments, a wristband, chestband, leg band, or other form of attachment may be employed. Although, it is understood that the above is merely one illustrative example to which the disclosed subject matter is not limited.

In such an embodiment, tactile feedback device 108A may be positioned on and represent the front of the user 102. Tactile feedback device 108E may be positioned on and represent the back of the user 102. And, tactile feedback devices 408A and 408B may represent the user 102's right and left, respectively. In an alternative embodiment, the wristband 408B may contain multiple tactile feedback devices, physically separated from the plurality of sensors and controlled by the processor 110, to indicate direction without relying on other body locations for placement of the feedback devices. In this embodiment, wristband 408A may not be necessary, and feedback device 108A could be programmed to indicate the magnitude of the radiation field strength and alert the user to certain levels associated with radiation control (e.g., boundaries defined for specific purposes) and radiation safety.

In various embodiments, detached tactile feedback devices may be worn on the user 102's legs or head. In such an embodiment, the detached tactile feedback devices may be coupled with a hat, helmet, shoes, boots, or socks, etc.

Figure 5:
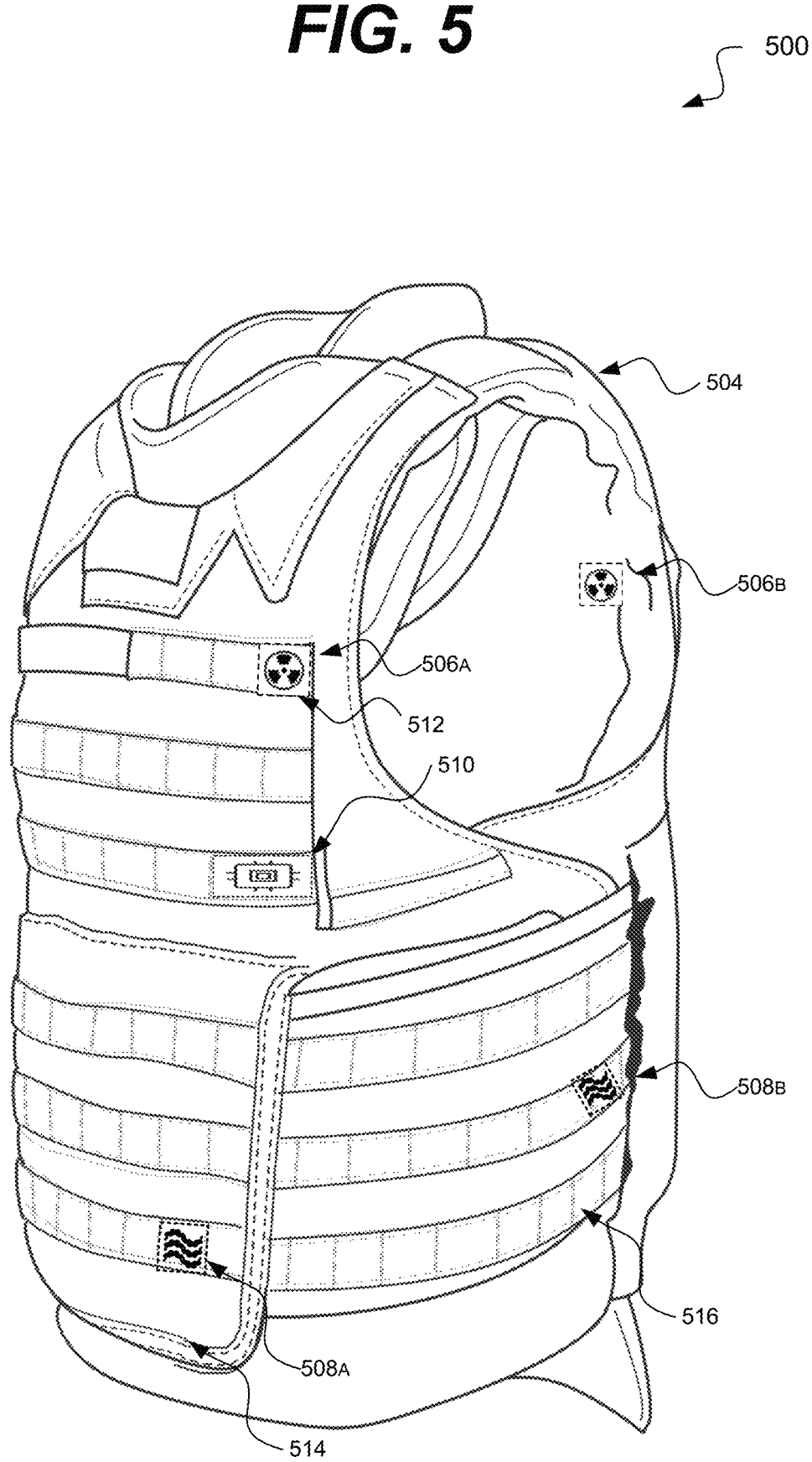
FIG. 5 is a diagram of an example embodiment of a system in accordance with the disclosed subject matter.

FIG. 5 is a diagram of an example embodiment of a system 500 in accordance with the disclosed subject matter. In various embodiments, the system 500 may be worn, used, or employed by law enforcement (LE), by the military, by other government agents, or by civilians. In such an embodiment, the system 500 may facilitate the detection and location of one or more substances (e.g., a radiation source).

In various embodiments, the system 500 may include a garment or tactical vest 504, sensors 506 (e.g., sensors 506A and 506B), tactile feedback devices 508 (devices 508A and 508B) and a processing circuit 510. In various embodiments, the system 500 may include additional sensors 506 and/or tactical feedback devices 508 that are not shown due to the orientation of the vest 504. It is understood that the above are merely a few illustrative examples to which the disclosed subject matter is not limited.

In the illustrated embodiment, the vest 504 may include a plurality of pouches or pockets 512. Each pouch 512 may be configured to hold, store, or mount a sensor 506. In some embodiments, the pouches 512 may be configured to hold, store, or mount a tactile feedback device 508 and/or processing circuit 510.

In various embodiments, the sensors 506 and/or tactile feedback devices 508 may be sewn into or otherwise fixedly coupled with the vest 504. Sensor 506A is shown on the outside of the vest 504. Whereas, sensor 506B is shown as being mounted inside the vest 504. In such an embodiment, the vest 504 may not shield the sensor 506B enough to substantially alter detection functions.

In the illustrated embodiment, one or more tactile feedback devices (e.g., device 508A) may be placed in a relatively non-movable or non-adjustable portion 514 of the vest 504 (e.g., the front left overhanging flap). In some embodiments, one or more tactile feedback devices (e.g., device 508B) may be placed in a relatively movable or adjustable portion 516 of the vest 504 (e.g., the left side Velcro strap). In such an embodiment, the user may position the tactile feedback device 508B for comfort and/or to increase feedback. For example, a user may wish to move the Velcro strap or tactile feedback device 508B to a portion of the user's left side where they will feel the feedback vibration better. It is understood that the above is merely one illustrative example to which the disclosed subject matter is not limited.

Figure 6:
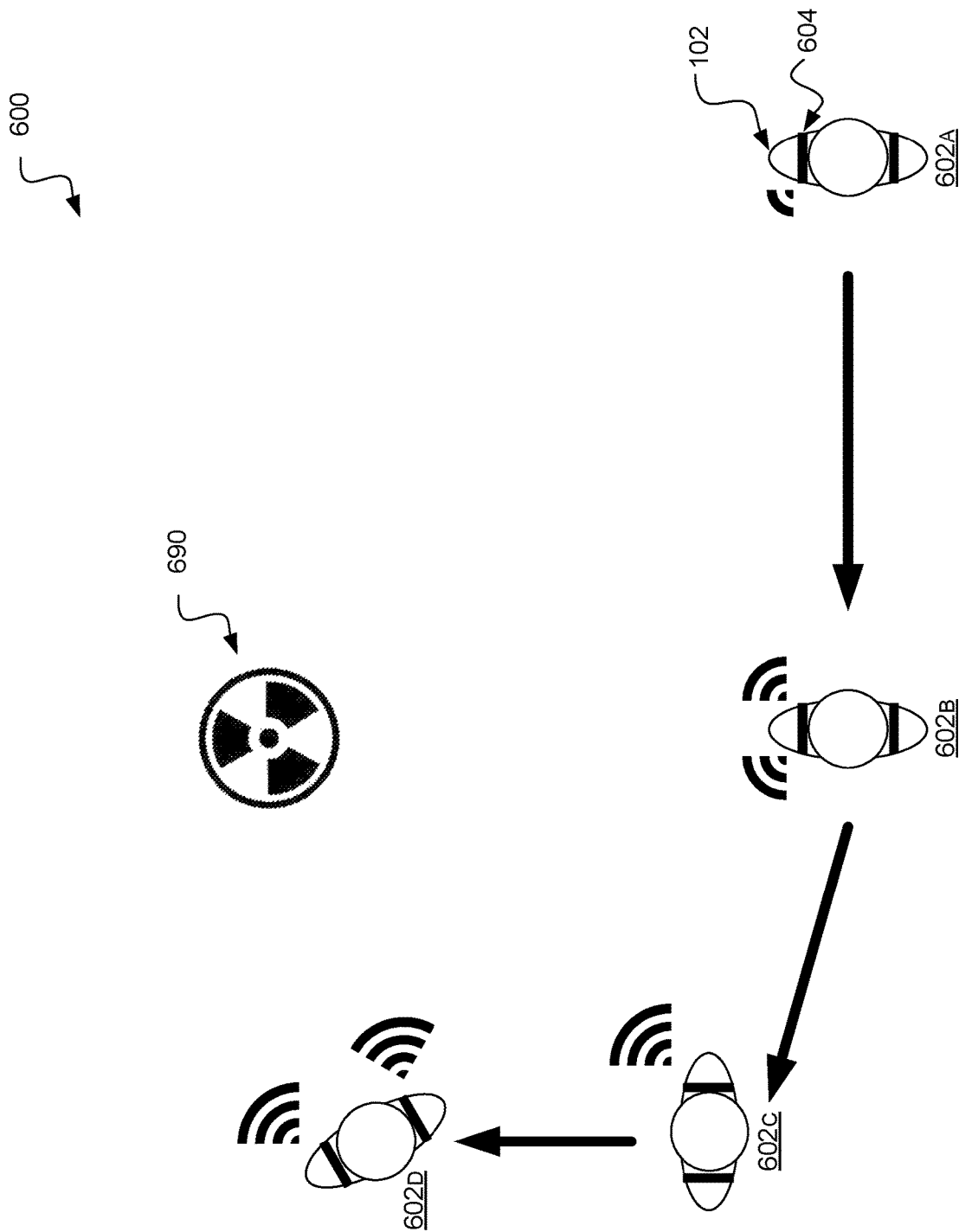
FIG. 6 is a diagram of an example embodiment of a system in accordance with the disclosed subject matter.

FIG. 6 is a diagram of an example embodiment of a system 600 in accordance with the disclosed subject matter. In various embodiments, the system 600 may show an example of a user 102 employing the passive radiation alerting and locating system 604 over a period of time.

In the illustrated embodiment, a user 102 may wear or employ a passive radiation alerting and locating system 604. As described above, this passive radiation alerting and locating system 604 may include a garment, sensors, tactile feedback devices, etc. FIG. 6 shows the user 102 walking around a radiation source 690 over a period of time. The user 102 may start at position 602A, move to position 602B, then 602C, and finally position 602D. It is understood that the above is merely one illustrative example to which the disclosed subject matter is not limited.

As described above, the user 102 may have initiated or calibrated the passive radiation alerting and locating system 604 to set a baseline level of radiation. In such an embodiment, if the passive radiation alerting and locating system 604 does not detect a level of radiation rising above a threshold set, in part, by the baseline radiation then the tactile feedback devices will not provide feedback (e.g., vibrate).

In the illustrated embodiment, at position 602A the user 102 (and sensors) are farthest away from the radiation source 690. The radiation source 690 is generally to the user 102's front right. In such an embodiment, assuming the four-point constellation of FIG. 1, the front left, and back sensors may not detect enough radiation to trigger the threshold and those feedback devices may remain inert. However, the front right sensor may detect a level sufficient to trigger the lowest threshold, threshold above background, or relative response compared to the other sensors as interpreted by the processor so that the front right feedback device may begin to vibrate. This may alert the user 102 that the radiation source 690 is towards the user 102's front right and not very strong (maybe far away).

In the illustrated embodiment, as the user 102 walks to position 602B the radiation source 690 may now be closer and directly to the user 102's right. As such, while the left sensors may be shielded to greater extent and hence their associated feedback devices may be motionless to low-level intensity as dictated by the processor for all sensors, the front and back sensors may detect an equal level of intensity. Both front and back feedback devices may vibrate at a level intensity corresponding to the detected radiation levels or not at all depending on the sensitivity settings of the processor. The processor controls the feedback intensity delivered by each device considering the magnitude and relative intensity recorded by all sensors.

In the illustrated embodiment, as the user 102 walks to position 602C the radiation source 690 may now be closer and again to the user 102's front right. As such, the front left, and back sensors may not detect enough radiation to trigger the threshold and their associated feedback devices may remain inert. Or, in another embodiment, they may be close enough to detect the radiation, just at a lower level than the front right sensor. In such an embodiment, their feedback devices may vibrate at a lower level of intensity. However, the front right sensor may detect the radiation at a level sufficient to trigger the highest threshold, and the front right feedback device may begin to vibrate at a corresponding rate as dictated by the processor. This may alert the user 102 that the radiation source 690 is towards the user 102's front right and strong (maybe closer than at position 602A).

In the illustrated embodiment, as the user 102 walks to position 602D, the radiation source 690 may now be even closer and to the user 102's front. As such, the back sensors may not detect enough radiation to trigger the threshold (e.g., as determined by the processing circuit) and those feedback devices may remain inert. Or they may be close enough to detect the radiation, just at a lower level than the front right sensor. In such an embodiment, their feedback devices may vibrate at a lower level of intensity. However, the front sensors may detect a level sufficient to trigger the highest threshold and the front feedback devices may begin to vibrate at a corresponding rate. This may alert the user 102 that the radiation source 690 is towards the user 102's front and strong (maybe closer than at position 602A).

It is understood that the above are merely a few illustrative examples to which the disclosed subject matter is not limited. In such an embodiment, a user 102 may take a number of different paths and be alerted to the direction and intensity of any detected radiation source 690 or other NBC source.

Figure 7:
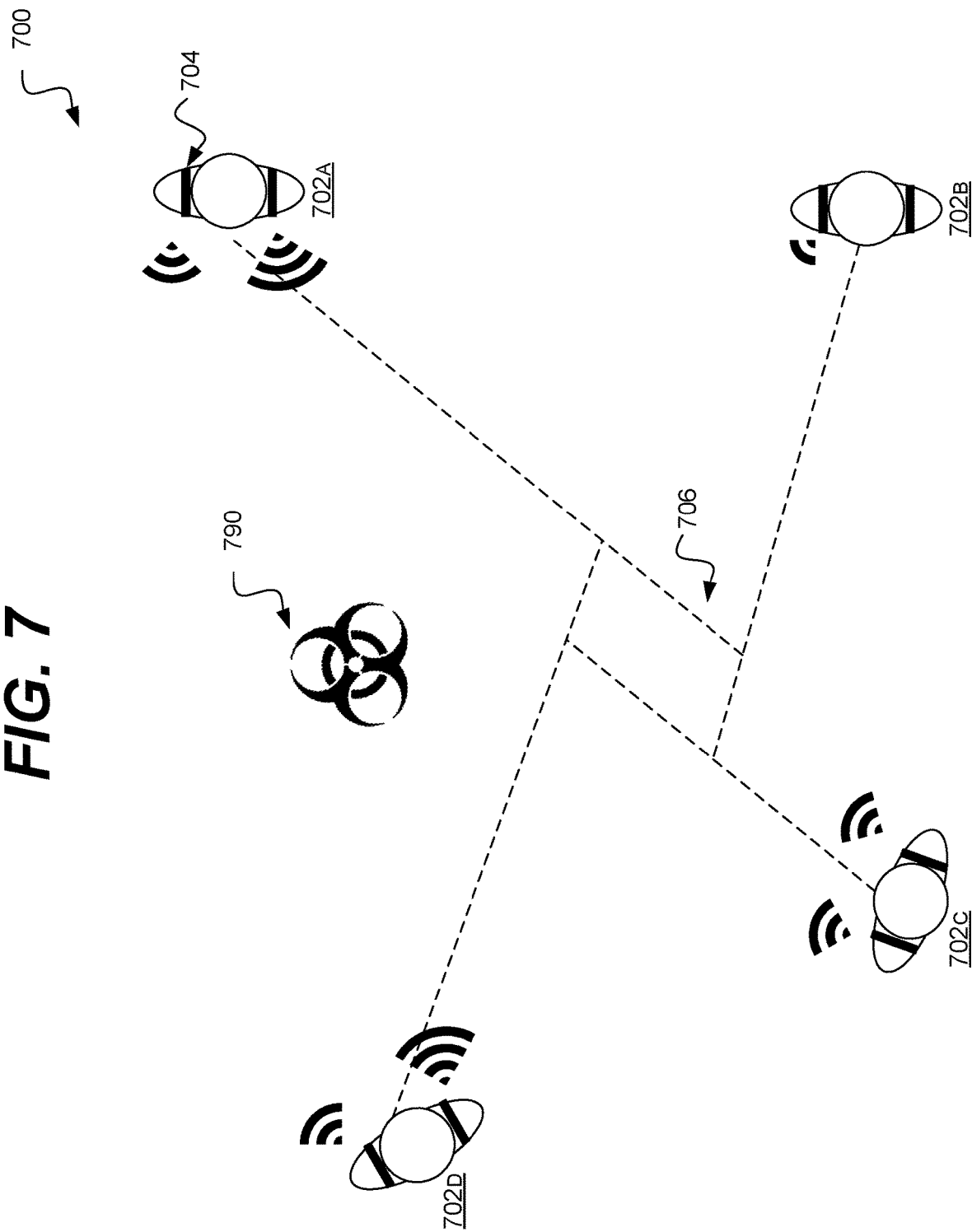
FIG. 7 is a diagram of an example embodiment of a system in accordance with the disclosed subject matter.

FIG. 7 is a diagram of an example embodiment of a system 700 in accordance with the disclosed subject matter. In various embodiments, the system 700 may show a plurality of users employing the passive radiation alerting and locating system 104, each with processors designed to differentiate signals from each system.

In the illustrated embodiment, a group of users (e.g. user 702A, 702B, 702C, and 702D) may wear or employ their respective passive radiation alerting and locating systems 704. As described above, these passive radiation alerting and locating systems 704 may include a garment, sensors, tactile feedback devices, etc. FIG. 7 shows the users 702 positioned around a biological source 790. It is understood that the above is merely one illustrative example to which the disclosed subject matter is not limited.

In the illustrated embodiment, four users (e.g. users 702A, 702B, 702C, and 702D) are attempting to find a biological source 790. As described above, in various embodiments, the source may be radiological, chemical, biological, etc. In some embodiments, such a source (e.g., an NBC source, etc.) may be generically described as a contaminating source, or source of contamination. These users 702 have happened, in this example, to have taken various positions roughly in the shape of a trapezoid around the biological source 790. The users 702 are generally facing the biological source 790 at different orientations and at different distances.

For example, user 702A is positioned with the source in front and slightly to the left, and user 702A's feedback devices are vibrating on the front and more heavily towards user 702A's left. User 702B is positioned with the source to the right and slightly to the front, and user 702B's feedback devices are vibrating on the right front. User 702C is positioned with the source directly to the front, and user 702C's feedback devices are vibrating on the front. User 702D is positioned with the source to the front and slightly to the right, and relatively close, and user 702B's feedback devices are strongly vibrating on the right front.

In various embodiments, the passive radiation alerting and locating systems 704 may be equipped (e.g., via the processing circuit) with a form of wireless communication 706 (e.g., Wi-If, cellular, etc.). In such an embodiment, passive radiation alerting and locating systems 704 may be able to receive and transmit detection information (e.g., direction, level or intensity, etc.) between each other. In various embodiments, this may occur via an ad hoc network.

In such an embodiment, each processing circuit of the respective passive radiation alerting and locating systems 704 may be configured to adjust its own estimation of the direction of the biological source 790 based, at least in part, on the detection information provided by the other user 702's respective passive radiation alerting and locating systems 704. In such an embodiment for the described system, a unique form of triangulation may be performed.

In one embodiment, this additional information may be employed to improve the accuracy of the feedback devices. In another embodiment, the results of this triangulation may appear via a screen on the processing circuit, passive radiation alerting and locating systems 704, or a central processing circuit.

In some embodiments, the passive radiation alerting and locating systems 704 may include an absolute positional device (e.g., a global positioning system (GPS) circuit, etc.). In such an embodiment, the GPS, absolute position, or location information may be transmitted via the wireless communications 706 as part of or with the detection information. In such an embodiment, the passive radiation alerting and locating systems 704 may consider the GPS or other positional information during the triangulation process. In various embodiments, the passive radiation alerting and locating systems 704 may display an estimation of the location of the biological source 790 to the user 702. In various embodiments, this position may be displayed via a screen of the processing circuit (e.g., on a smartphone). In some embodiments, the estimated absolute position of the biological source 790 may not be passively communicated to the user 702.

In another embodiment, the wireless communications 706 may communicate with a command center or base (not shown). In such an embodiment, a tactical officer or commander may be shown the estimated absolute position of the biological source 790 (e.g., via a large screen wall display). The tactical officer or commander may then radio information as they see fit back to the users 702. In one embodiment, the users 702 may carry a radio or telephone (e.g., a cellphone, an earpiece, etc.). It is understood that the above is merely one illustrative example to which the disclosed subject matter is not limited.

In another embodiment, the passive radiation alerting and locating systems 704 may communicate with the command center or base, not for purposes of triangulation. Instead, each passive radiation alerting and locating system 704 may communicate detection information and/or positional information to the command center or base for other purposes (e.g., recordkeeping, archiving, etc.). It is understood that the above are merely a few illustrative examples to which the disclosed subject matter is not limited.

Figure 8:
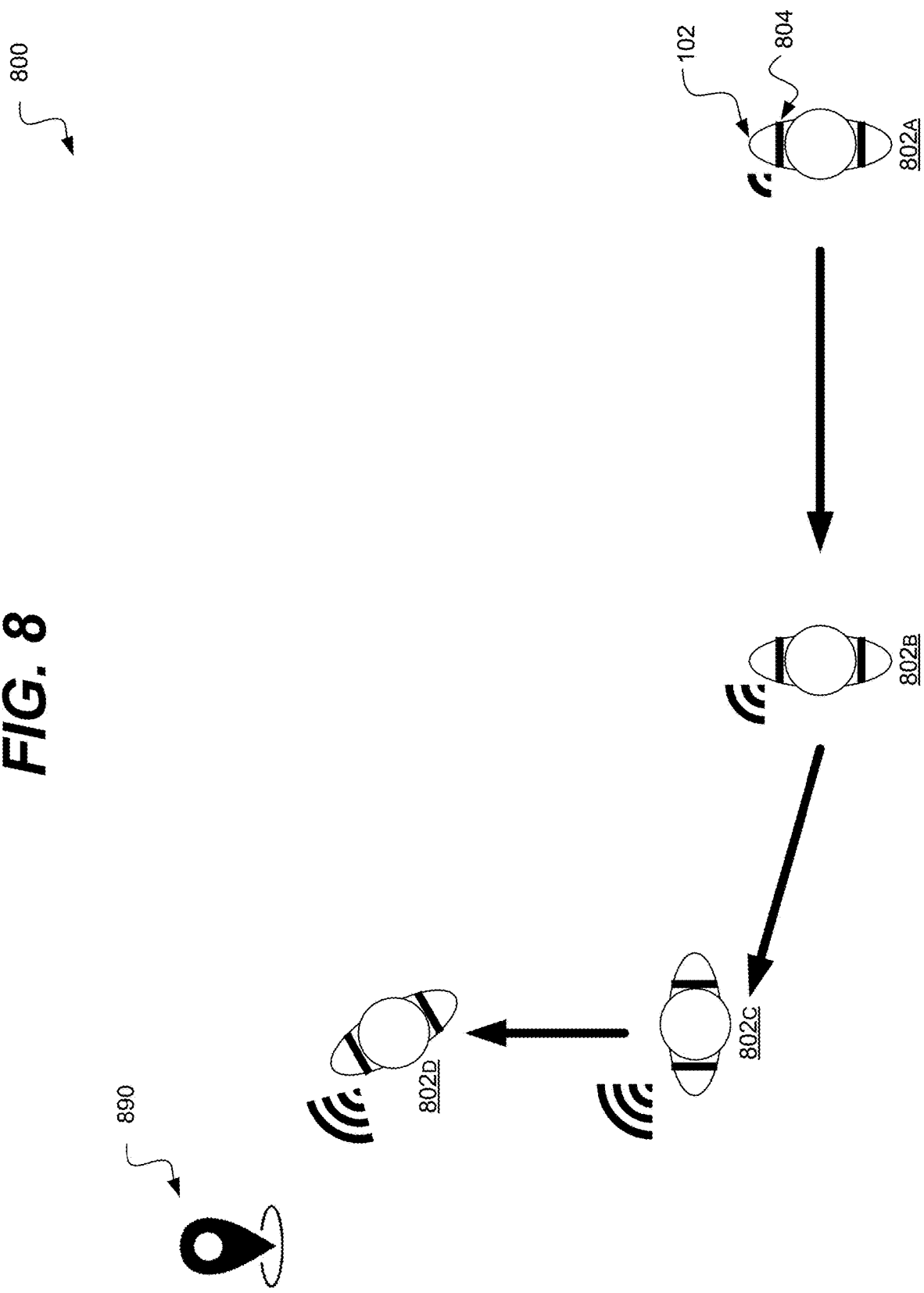
FIG. 8 is a diagram of an example embodiment of a system in accordance with the disclosed subject matter.

FIG. 8 is a diagram of an example embodiment of a system 800 in accordance with the disclosed subject matter. In various embodiments, the system 800 may show an example of a user 102 employing the passive locating system 804 over a period of time.

In the illustrated embodiment, a user 102 may wear or employ a passive locating system 804. As described above, this passive locating system 804 may include a garment, sensors, tactile feedback devices, etc. In the illustrated embodiment, the passive locating system 804 may not include radiation or NBC detection capabilities. Instead, the passive locating system 804 may include location sensor(s) that may detect satellite-based location signals (e.g., Global Positioning System (GPS), Russian Global Navigation Satellite System (GLONASS), Galileo or global navigation satellite system (GNSS), BeiDou Navigation Satellite System (BDS), Indian Regional Navigation Satellite System (IRNSS or NAVIC), Quasi-Zenith Satellite System (QZSS), etc.). In another embodiment, the location sensor(s) may include non-satellite based sensor(s).

FIG. 8 shows the user 102 walking around a location 890 over a period of time. The user 102 may start at position 802A, move to position 802B, then 802C, and finally position 802D. It is understood that the above is merely one illustrative example to which the disclosed subject matter is not limited.

As described above, the user 102 may have determined a location 890 that the passive locating system 804 may guide the user 102 to. In various embodiments, the location 890 may be set by the user 102. In another embodiment, the location 890 may be received by the passive locating system 804 (e.g., via a message from an external system, such as for example, another user's cell phone, a tracking beacon, etc.).

In the illustrated embodiment, at position 802A the user 102 (and sensors) are farthest away from the location 890. The location 890 is generally to the user 102's front right. In such an embodiment, the sensor(s) may determine the user 102's location. The processing unit may compute the difference between the user 102's location and the location 890. Based upon the direction to the location 890 and orientation of the user 102, the tactical feedback unit(s) of the passive locating system 804 may vibrate or otherwise provide feedback. This may alert the user 102 that the location 890 is towards the user 102's front right and not very strong (maybe far away).

In the illustrated embodiment, as the user 102 walks to position 802B the location 890 may now be closer and directly to user 102. As such, while the left and back feedback devices may be motionless or at low-level of intensity. The front right feedback device may vibrate at a level intensity corresponding to the detected distance from the location 890. The processor controls the feedback intensity delivered by each device considering the distance and direction from the location 890.

In the illustrated embodiment, as the user 102 walks to position 802C the location 890 may now be closer and now to the user 102's front left. As such, the front right, and back sensors may not trigger and their associated feedback devices may remain inert. However, the front left feedback device may begin to vibrate at a corresponding rate as dictated by the processor. This may alert the user 102 that the location 890 is towards the user 102's front left and close.

In the illustrated embodiment, as the user 102 walks to position 802D, the location 890 may now be even closer but the user 102 may have turned their back to it. As such, the back feedback device (e.g., the back left device) may vibrate. However, the front feedback devices (and the back, right device) may remain inert. This may alert the user 102 that the location 890 is behind the user 102's left side.

It is understood that the above are merely a few illustrative examples to which the disclosed subject matter is not limited. In such an embodiment, a user 102 may take a number of different paths and be alerted to the direction and intensity of any detected location 890 or other NBC source.

Figure 9:
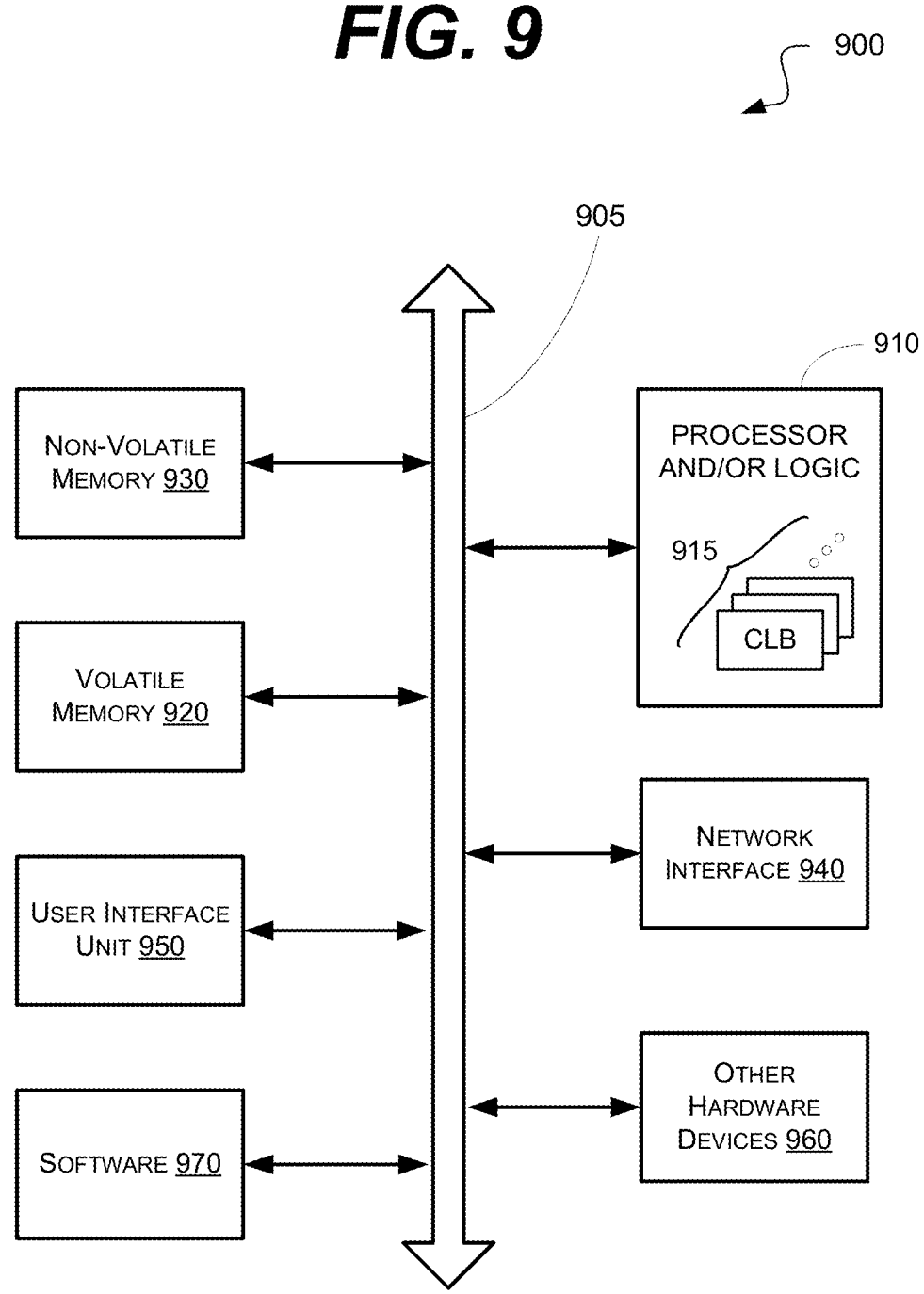
FIG. 9 is a schematic block diagram of an information processing system that may include devices formed according to principles of the disclosed subject matter.

FIG. 9 is a schematic block diagram of an information processing system 900, which may include semiconductor devices. In various embodiments, such information processing system 900 may be included by or employed according to principles of the disclosed subject matter.

Referring to FIG. 9, an information processing system 900 may include one or more of devices constructed according to the principles of the disclosed subject matter. In another embodiment, the information processing system 900 may employ or execute one or more techniques according to the principles of the disclosed subject matter.

In various embodiments, the information processing system 900 may include a computing device, such as, for example, a laptop, desktop, workstation, server, blade server, personal digital assistant, smartphone, tablet, and other appropriate computers or a virtual machine or virtual computing device thereof. In various embodiments, the information processing system 900 may be used by a user (not shown).

The information processing system 900 according to the disclosed subject matter may further include a central processing unit (CPU), logic, or processor 910. In some embodiments, the processor 910 may include one or more functional unit blocks (FUBs) or combinational logic blocks (CLBs) 915. In such an embodiment, a combinational logic block may include various Boolean logic operations (e.g., NAND, NOR, NOT, XOR), stabilizing logic devices (e.g., flip-flops, latches), other logic devices, or a combination thereof. These combinational logic operations may be configured in simple or complex fashion to process input signals to achieve a desired result. It is understood that while a few illustrative examples of synchronous combinational logic operations are described, the disclosed subject matter is not so limited and may include asynchronous operations, or a mixture thereof. In one embodiment, the combinational logic operations may comprise a plurality of complementary metal oxide semiconductors (CMOS) transistors. In various embodiments, these CMOS transistors may be arranged into gates that perform the logical operations; although it is understood that other technologies may be used and are within the scope of the disclosed subject matter.

The information processing system 900 according to the disclosed subject matter may further include a volatile memory 920 (e.g., a Random Access Memory (RAM)). The information processing system 900 according to the disclosed subject matter may further include a non-volatile memory 930 (e.g., a hard drive, an optical memory, a NAND or Flash memory). In some embodiments, either the volatile memory 920, the non-volatile memory 930, or a combination or portions thereof may be referred to as a "storage medium". In various embodiments, the volatile memory 920 and/or the non-volatile memory 930 may be configured to store data in a semi-permanent or substantially permanent form.

In various embodiments, the information processing system 900 may include one or more network interfaces 940 configured to allow the information processing system 900 to be part of and communicate via a communications network. Examples of a Wi-Fi protocol may include, but are not limited to, Institute of Electrical and Electronics Engineers (IEEE) 802.11g, IEEE 802.11n. Examples of a cellular protocol may include, but are not limited to: IEEE 802.16m (a.k.a. Wireless-MAN (Metropolitan Area Network) Advanced, Long Term Evolution (LTE) Advanced, Enhanced Data rates for GSM (Global System for Mobile Communications) Evolution (EDGE), Evolved High-Speed Packet Access (HSPA+). Examples of a wired protocol may include, but are not limited to, IEEE 802.3 (a.k.a. Ethernet), Fibre Channel, Power Line communication (e.g., Home-Plug, IEEE 1901). It is understood that the above are merely a few illustrative examples to which the disclosed subject matter is not limited.

The information processing system 900 according to the disclosed subject matter may further include a user interface unit 950 (e.g., a display adapter, a haptic interface, a human interface device). In various embodiments, this user interface unit 950 may be configured to either receive input from a user and/or provide output to a user. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

In various embodiments, the information processing system 900 may include one or more other devices or hardware components 960 (e.g., a display or monitor, a keyboard, a mouse, a camera, a fingerprint reader, a video processor). It is understood that the above are merely a few illustrative examples to which the disclosed subject matter is not limited.

The information processing system 900 according to the disclosed subject matter may further include one or more system buses 905. In such an embodiment, the system bus 905 may be configured to communicatively couple the processor 910, the volatile memory 920, the non-volatile memory 930, the network interface 940, the user interface unit 950, and one or more hardware components 960. Data processed by the processor 910 or data inputted from outside of the non-volatile memory 930 may be stored in either the non-volatile memory 930 or the volatile memory 920.

In various embodiments, the information processing system 900 may include or execute one or more software components 970. In some embodiments, the software components 970 may include an operating system (OS) and/or an application. In some embodiments, the OS may be configured to provide one or more services to an application and manage or act as an intermediary between the application and the various hardware components (e.g., the processor 910, a network interface 940) of the information processing system 900. In such an embodiment, the information processing system 900 may include one or more native applications, which may be installed locally (e.g., within the non-volatile memory 930) and configured to be executed directly by the processor 910 and directly interact with the OS. In such an embodiment, the native applications may include pre-compiled machine executable code. In some embodiments, the native applications may include a script interpreter (e.g., C shell (csh), AppleScript, AutoHotkey) or a virtual execution machine (VM) (e.g., the Java Virtual Machine, the Microsoft Common Language Runtime) that are configured to translate source or object code into executable code which is then executed by the processor 910.

The semiconductor devices described above may be encapsulated using various packaging techniques. For example, semiconductor devices constructed according to principles of the disclosed subject matter may be encapsulated using any one of a package on package (POP) technique, a ball grid arrays (BGAs) technique, a chip scale packages (CSPs) technique, a plastic leaded chip carrier (PLCC) technique, a plastic dual in-line package (PDIP) technique, a die in waffle pack technique, a die in wafer form technique, a chip on board (COB) technique, a ceramic dual in-line package (CERDIP) technique, a plastic metric quad flat package (PMQFP) technique, a plastic quad flat package (PQFP) technique, a small outline package (SOIC) technique, a shrink small outline package (SSOP) technique, a thin small outline package (TSOP) technique, a thin quad flat package (TQFP) technique, a system in package (SIP) technique, a multi-chip package (MCP) technique, a wafer-level fabricated package (WFP) technique, a wafer-level processed stack package (WSP) technique, or other technique as will be known to those skilled in the art.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

In various embodiments, a computer readable medium may include instructions that, when executed, cause a device to perform at least a portion of the method steps. In some embodiments, the computer readable medium may be included in a magnetic medium, optical medium, other medium, or a combination thereof (e.g., CD-ROM, hard drive, a read-only memory, a flash drive). In such an embodiment, the computer readable medium may be a tangibly and non-transitorily embodied article of manufacture.

While the principles of the disclosed subject matter have been described with reference to example embodiments, it will be apparent to those skilled in the art that various changes and modifications may be made thereto without departing from the spirit and scope of these disclosed concepts. Therefore, it should be understood that the above embodiments are not limiting, but are illustrative only. Thus, the scope of the disclosed concepts are to be determined by the broadest permissible interpretation of the following claims and their equivalents, and should not be restricted or limited by the foregoing description. It is, therefore, to be understood that the appended claims are intended to cover all such modifications and changes as fall within the scope of the embodiments.

What is claimed is:

1. An apparatus comprising:
a plurality of sensors configured to detect a presence of a source of radiation; and
a garment configured to be worn by a user, wherein the garment comprises
a plurality of feedback devices configured to automatically indicate, simultaneously via at least two feedback devices, to the user a direction of the source of radiation; and
wherein the apparatus is configured to:
detect a first level of radiation at a first sensor and a second level of radiation at a second sensor,
vibrate a first feedback device at a first level of intensity, wherein the first feedback device is associated with the first sensor, and
vibrate a second feedback device at a second level of intensity, wherein the second feedback device is associated with the second sensor.

2. The apparatus of claim 1, further comprising a processing circuit configured to:
determine a level of background radiation; and
adjust a detected level of radiation based, at least in part, upon the level of background radiation.

3. The apparatus of claim 1, further comprising a processing circuit configured to:
determine whether the plurality of sensors detect a level of radiation greater than an adjustable threshold value;
control the feedback devices based, at least in part, on an output of at least one sensor; and
if not, preventing the feedback devices from indicating the direction of the source of radiation.

4. The apparatus of claim 1, wherein the plurality of tactile feedback devices are distributed in a constellation that provides at least three directions of tactile feedback.

5. The apparatus of claim 1, wherein the plurality of sensors are coupled with the garment, and arranged in a constellation that facilitates detection of radiation in at least three directions.

6. The apparatus of claim 5, wherein the garment includes a plurality of pouches, each pouch configured to hold a respective sensor.

7. The apparatus of claim 5, wherein at least a portion of the plurality of sensors are attached to a rod configured to elevate at least a portion of the sensors above a head of the user.

8. The apparatus of claim 1, wherein the feedback devices are configured to:
vary a level of feedback intensity in correlation with a detected strength of the source of radiation.

9. The apparatus of claim 1, further comprising a processor configured to vary the intensity of vibration based, at least partially, on a level of detected radiation to indicate the direction of the source of radiation by simultaneously vibrating the two or more of the feedback devices.

10. The apparatus of claim 1, further comprising a processing circuit configured to:
associate each feedback device with one or more corresponding sensors;
determine, for each sensor, a detected level of radiation;
determine, for each feedback device, which of a plurality of threshold ranges the detected level of radiation associated with the corresponding sensors falls; and
instruct, each feedback device, to indicate to the user the respective threshold range of the detected level of radiation associated with the corresponding sensors.

11. A system comprising:
a plurality of sensors configured to detect a presence of, at least one of, a source of contamination;
a processing circuit configured to determine a level of baseline contamination level; and
a plurality of feedback devices configured to:
be worn by a user, and
automatically, and at least partially passively, indicate, simultaneously via at least two feedback devices, to the user a direction of the source of contamination, wherein the plurality of feedback devices are configured to vary an intensity of vibration based, at least partially, on a level of detected contamination; and wherein the apparatus is configured to:
  detect a first level of contamination at a first sensor and a second level of contamination at a second sensor,
  vibrate a first feedback device at a first level of intensity, wherein the first feedback device is associated with the first sensor, and
  vibrate a second feedback device at a second level of intensity, wherein the second feedback device is associated with the second sensor.

12. The system of claim 11, wherein the processing circuit is configured to:
  map each feedback device with one or more corresponding sensor, and
  if a direction of the plurality of sensors changes, in respect to a direction of the feedback device, remap each feedback device with the sensors; and
wherein the plurality of sensors are configured to detect a presence of, at least, a first source of contamination and a second source of contamination, wherein the type of the first and second sources of contamination are selected from a group consisting of: a radiological source, a biological source, and a chemical source.

13. The system of claim 11, wherein the processing circuit is configured to:
  adjust a response of each feedback device based, at least in part, upon a level of detected contamination associated with the respective feedback device.

14. The system of claim 11, wherein the plurality of feedback devices comprises:
  a first set of feedback device(s) configured to provide feedback to the user via a first form of indication, and
  a second set of feedback device(s) configured to provide feedback to the user via a second form of indication.

15. The system of claim 14, wherein the first set of feedback device(s) is configured to provide feedback to the user via vibration, and
  wherein the second set of feedback device(s) is configured to provide additional feedback to the user via light.

16. The system of claim 14, wherein the first set of feedback device(s) is configured to, for each of the first set of feedback device(s), provide feedback to the user when the detected level of contamination associated with the respective feedback device exceeds a first threshold value; and
  wherein the second set of feedback device(s) is configured to, for each of the second set of device(s), provide feedback to the user when the detected level of contamination associated with the respective feedback device exceeds a second threshold value.

17. The system of claim 11, wherein at least a portion of the plurality of sensors are coupled with a sensor pod, and wherein the sensor pod is coupled with a mechanical conveyance.

18. The system of claim 11, further comprising a plurality of garments; and
  wherein each feedback device is coupled with a respective garment.

19. A system comprising:
  a plurality of passive radiation alerting and locating systems, each passive radiation alerting and locating system, at least partially, worn by a respective user;
  wherein each passive radiation alerting and locating system comprises:
    a plurality of sensors configured to detect a direction of a source of radiation,
    a processing circuit configured to determine a level of baseline radiation and control, at least in part, a plurality of feedback devices, and
    the plurality of feedback devices are configured to automatically, and at least partially passively, indicate to the user, via at least two simultaneously active feedback devices, the direction of the source of radiation, wherein each of the plurality of feedback devices are configured to each vary an intensity of an indication based on a level of detected radiation by a sensor associated with the respective feedback device; and
  wherein each passive radiation alerting and locating system is configured to:
    detect a first level of radiation at a first sensor and a second level of radiation at a second sensor,
    vibrate a first feedback device at a first level of intensity, wherein the first feedback device is associated with the first sensor, and
    vibrate a second feedback device at a second level of intensity, wherein the second feedback device is associated with the second sensor; and
  wherein the plurality of passive radiation alerting and locating systems are configured to communicate detection information amongst one another.

20. The system of claim 19, wherein the processing circuit is configured to:
  determine a location of the processing circuit's passive radiation alerting and locating system;
  receive detection information and location information from another passive radiation alerting and locating system;
  adjust an indication provided by the plurality of feedback devices based, at least in part, upon the direction of the source of radiation provided by the plurality of sensors, the location determined by the processing circuit, and the detection information and location information from the other passive radiation alerting and locating system.

* * * * *